United States Patent
Brossia et al.

(10) Patent No.: US 6,925,888 B2
(45) Date of Patent: Aug. 9, 2005

(54) MEMS SENSOR FOR DETECTING STRESS CORROSION CRACKING

(75) Inventors: Christopher S. Brossia, San Antonio, TX (US); Heather S. Hanson, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 0 days.

(21) Appl. No.: 10/782,011

(22) Filed: Feb. 19, 2004

(65) Prior Publication Data

US 2004/0200295 A1 Oct. 14, 2004

Related U.S. Application Data

(60) Provisional application No. 60/450,862, filed on Feb. 28, 2003.

(51) Int. Cl.[7] .............................................. G01N 19/08
(52) U.S. Cl. ......................................... 73/799; 73/777
(58) Field of Search ................... 73/777, 799, 862.639, 73/790, 826, 788

(56) References Cited

U.S. PATENT DOCUMENTS

| | | | | |
|---|---|---|---|---|
| 5,596,194 A | * | 1/1997 | Kubena et al. | 250/306 |
| 5,610,335 A | * | 3/1997 | Shaw et al. | 73/514.36 |
| 5,847,454 A | * | 12/1998 | Shaw et al. | 257/734 |
| 6,040,611 A | * | 3/2000 | De Los Santos et al. | 257/415 |
| 6,206,290 B1 | * | 3/2001 | Giebel et al. | 235/462.36 |
| 6,541,831 B2 | * | 4/2003 | Lee et al. | 257/415 |
| 6,619,123 B2 | * | 9/2003 | Gianchandani et al. | 73/514.29 |
| 6,692,145 B2 | * | 2/2004 | Gianchandani et al. | 374/185 |

OTHER PUBLICATIONS

International Search Report for PCT/US04/04958 mailed Nov. 18, 2004.

* cited by examiner

*Primary Examiner*—Max Noori
(74) *Attorney, Agent, or Firm*—Baker Botts L.L.P.

(57) ABSTRACT

A sensor for measuring stress corrosion cracking and methods of using the sensor. The sensor is a MEMS device and has a cantilevered beam made from a material of interest. The sensor has on-chip electrical connections for measuring electrical characteristics that indicate cracking of the beam. The sensor may further have on-chip actuators for applying stress to the beam.

23 Claims, 4 Drawing Sheets

US 6,925,888 B2

MEMS SENSOR FOR DETECTING STRESS CORROSION CRACKING

RELATED PATENT APPLICATION

This application claims the benefit of U.S. Provisional Application Ser. No. 60/450,862 filed Feb. 28, 2003 and entitled "MEMS Sensor for Detecting Stress Corrosion Cracking".

TECHNICAL FIELD OF THE INVENTION

This invention relates to sensors for detecting the effects of stress and corrosion on materials, and more particularly to such a sensor made using MEMS technology.

BACKGROUND OF THE INVENTION

Many engineering structures are subjected to the simultaneous conditions of an applied stress (or load) and a corrosive environment. This combination of stress and corrosion can lead to material failures that might not occur from either condition alone, or that would take longer to occur from either condition alone. The resulting material failure is known as "stress corrosion cracking", and can cause structural failure of equipment such as boilers, pressure vessels, oil and gas piping, bridges, vehicles, and aircraft.

There are a number of existing methods for measuring susceptibility to stress corrosion cracking, and for measuring crack propagation rates. One limitation of existing methods is that their detection of crack propagation rates is limited. A typical limit of $10^{-11}$ meters per second is too high to determine whether stress corrosion cracking will lead to failure of highly resistive materials over a long time period. Another limitation of existing methods is that they are not easily implemented as sensors for real-time real-world monitoring.

DETAILED DESCRIPTION OF THE INVENTION

The following description is directed to sensors and methods for monitoring materials for stress corrosion cracking. The propagation of such cracking is detected and measured using MEMS (micro-electromechanical systems) sensors. The sensors are small and have broad application. They measure cracking that results from the combined effects of both stress and corrosion.

The various embodiments of the sensor all include a sample of the material of interest, in the form of a tiny cantilevered beam. This beam is designed to crack in response to the combination of stress applied to the beam and from being placed in a corrosive environment. The sensor further includes electrical connections for measuring the extent of any cracking in the beam, and may also include actuators used for applying stress to the beam. The beam, the electrical connections, and actuators are integrated on the substrate.

The sensors may be used in-situ, such as by placement in the same real world environment in which the material of interest is to be used. In this manner, the sensor's beam undergoes the corrosive effects of the environment of interest. The sensors may also be used "predictively" by being placed in an artificial environment that is similar to the conditions under which the material of interest would be used. In either case, the beam is subjected to environmental conditions that may cause it to undergo cracking.

Regardless of whether the environmental conditions are real-world or artificially induced, the beam is also mechanically stressed. The stress may be applied using on-chip actuators, or the sensor may be fabricated without actuators and the stress applied manually. The stress may also be the result of the fabrication process, i.e., residual stress.

The stress can be applied prior to, during, or after, the placement of a sensor in the environment of interest. When the beam is stressed prior to being subjected to environmental conditions, it is referred to as being "pre-stressed".

Figure 1:
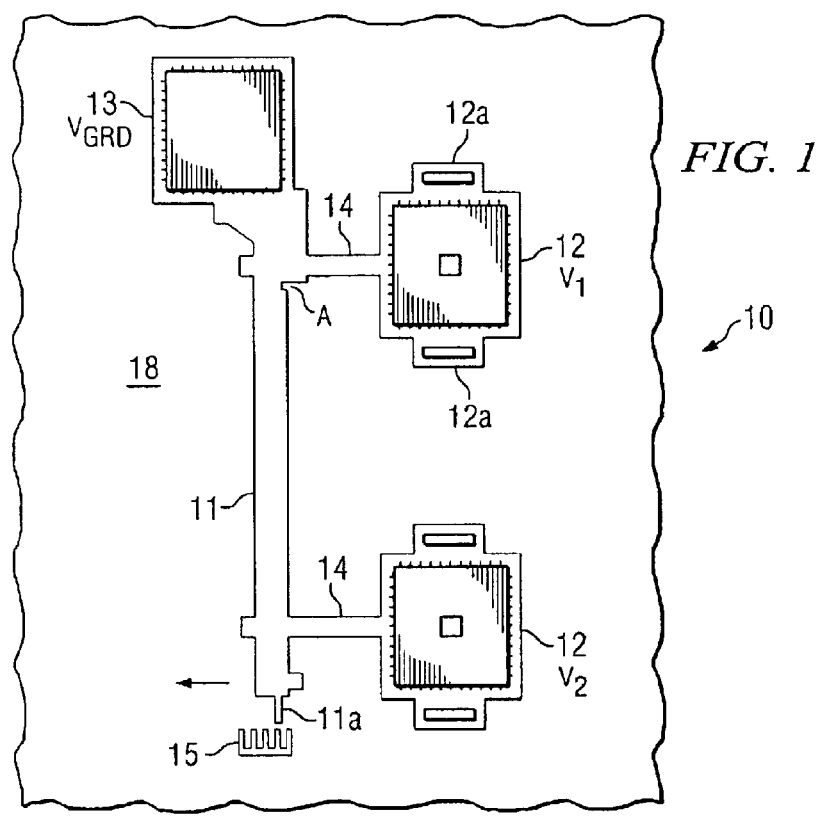
FIG. 1 is a plan view of a sensor in accordance with the invention, and having a "single arm" beam.

FIGS. 1–5 illustrate various embodiments of MEMS sensors in accordance with the invention. FIG. 1, and the other figures of this description, are plan views of a single sensor device ("chip"). It is assumed that each of these sensors includes, and is fabricated on, a substrate, such as substrate 18 of FIG. 1, using fabrication techniques known in the art of MEMS fabrication.

Referring to FIG. 1, sensor 10 is referred to herein as a "single arm" embodiment, and has a cantilevered beam 11. As stated above, beam 11 is fabricated from a material that is the same as the material of interest. For example, if the material of interest is used in an airplane structural member, such as a high strength aluminum alloy, beam 11 could be fabricated from aluminum. Alternatively, beam 11 may be fabricated from an analogous material, that is, a material that responds to stress and corrosion in the same manner as the material of interest. In the various embodiments of this description, it is assumed that the beam is electrically conductive, so that voltage can be applied to the beam for the purpose of resistive or capacitive measurements.

The fixed end of beam 11 is attached to pad 13. The free end of beam 11 is moveable across the surface of the substrate, as indicated by the arrow. Beam 11 is pre-notched at point A to encourage any cracking to occur at point A. To further encourage cracking only at point A, beam 11 is widened near its point of attachment to pad 13. In FIG. 1, beam 11 is notched at its right side, which implies that stress will be applied so as to move beam to the left, as indicated by the arrow.

The free end of beam 11 is narrowed to form a needle end 11a. As beam 11 moves to the left, needle 11a passes over a displacement scale 15. Scale 15 permits the displacement of beam 11 to be visually inspected, and thus the amount of stress placed on beam 11 to be measured.

Electrical contact pads 12 and 13 permit electrical connections to be made to beam 11, via electrical leads 14. Pad 13 is fixed, but pads 12 are moveable along the surface of sensor 10, in response to movement of beam 11. In other words, pads 12 "float" on the surface of the substrate 18, and are not fixed to the substrate. Guides 12a may be fabricated in a manner that constrains the movement of pads 12 to a plane slightly above the substrate and prevents vertical movement. In other embodiments, pads 12 may be tethered or otherwise attached to substrate 18, but in a manner that permits their electrical leads to follow movement of beam 11, if any.

In the embodiment of FIG. 1, sensor 10 does not include any actuators. Beam 11 is stressed manually, and as stated above, the application of stress and the exposure to environmental conditions need not occur simultaneously.

In operation, for measuring cracking as indicated by resistivity changes in beam 11, pad 13 connects beam 11 to ground. Pads 12 are used to measure a drop in applied voltage from one pad 12 to the other. When subjected to applied stress and to the corrosive effects of the environment, beam 11 will crack at point A. The air gap resulting from the crack increases the resistance of beam 11 from a point on one side of the crack to a point on the other side of the crack. Thus, if a pad 12 is placed on either side of the crack, changing voltage differences between them can be used to measure changes in resistance within beam 11. Thus, as the crack propagates, the cross sectional area of the metal available to carry current decreases and the measured resistance of the beam continues to increase proportionally.

Figure 2:
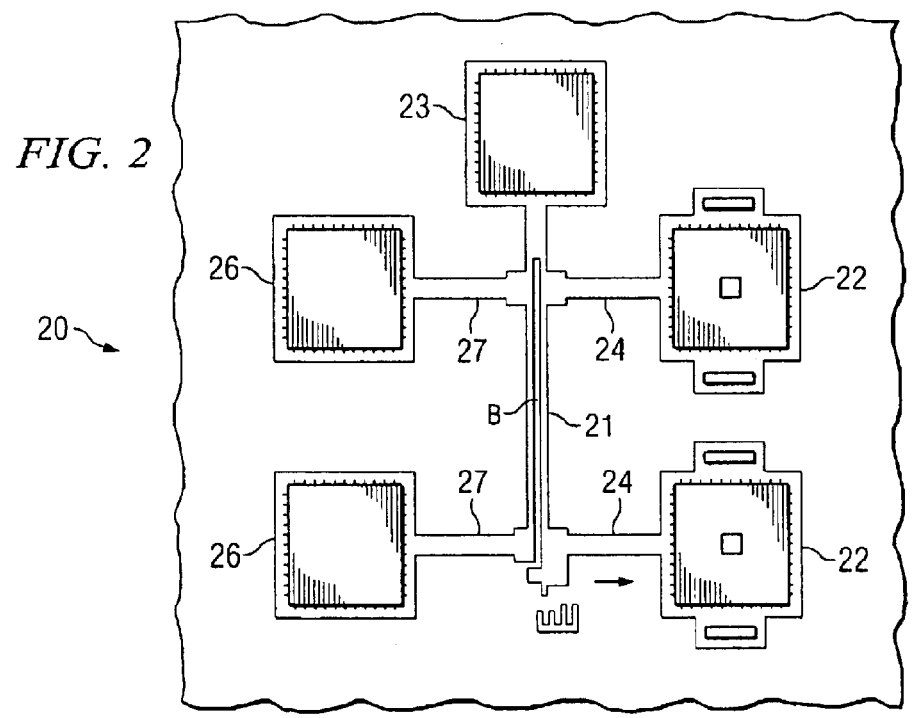
FIG. 2 is a plan view of a sensor in accordance with the invention, and having a "double arm" beam.

FIG. 2 illustrates a sensor 20 having a "double arm" beam 21. The right arm of beam 21 is intended to be pulled to the right, as indicated by the arrow in FIG. 2. The area of interest of beam 21 is at point B where the two arms meet. This is the area most likely to exhibit cracking as the result of the combined effects of the stress and corrosion.

Like sensor 10, sensor 20 is configured to measure changes in resistivity resulting from a decrease in cross sectional area of beam 21 associated with a propagating crack. FIG. 2 operates in a manner similar to FIG. 1, except that voltage is applied across two pairs of pads. Pad 23 is connected to ground. Pads 22 are moveable, but pads 26 need not be. Pads 22 have electrical leads 27 to the left arm of beam 21, and pads 26 have electrical leads 24 to the right arm of beam 21.

In operation, typically, the voltage is applied across pads 26 and across pads 22. The resistivity measurements measure resistance within either arm of beam 21 at different distances from the point of failure (the crack at point B).

Figure 3:
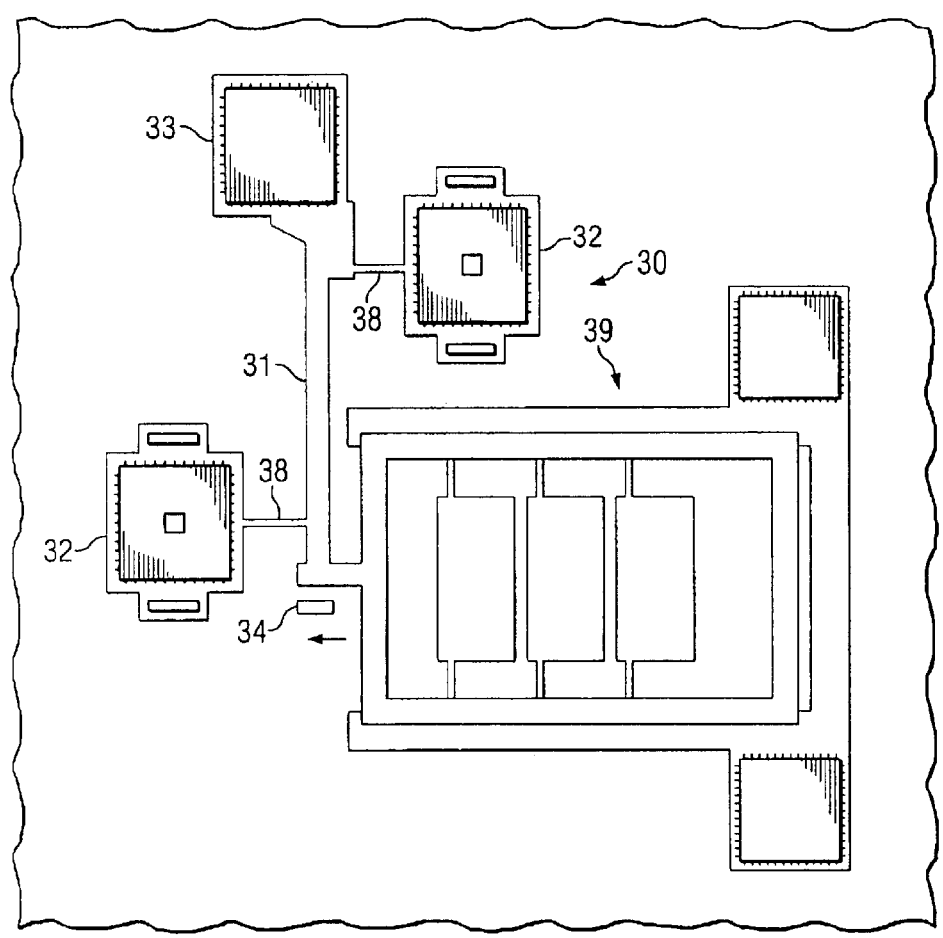
FIG. 3 illustrates a sensor with a single-arm beam and an on-chip actuator.

FIG. 3 illustrates a sensor 30, which has a single-arm beam 31, which is similar to that of sensor 10. However, sensor 30 includes an on-chip MEMS actuator 39. In the example of this description, actuator 39 is a scratch drive actuator, but many other types of actuators could be used.

In operation, actuator 39 is activated to apply force to beam 31, so as to push beam 31 in the horizontal direction, as indicated by the arrow in FIG. 3. Other actuators might operate differently so as to move beam 31 in either horizontal direction or in one or more vertical directions. The force may be applied and held, applied for a selected duration, or may be applied periodically.

Electrical leads 38 provide an electrical connection from beam 31 to electrical pads 32. In the example of FIG. 3, leads 38 are made from a metal such as gold, and are thinner than the leads of FIGS. 1 and 2, which are made from metal and polysilicon.

As in the embodiment of FIG. 1, pad 33 is fixed and pads 32 are moveable across the substrate. Pad 33 is connected to ground and a voltage is applied across pads 32. Changes in resistivity indicate the extent of cracking.

Changes in the load applied by actuator 39 necessary to maintain a specific displacement of beam 31 can be measured. This may be accomplished by determining the voltage or current consumed by the actuator 39, or by inspecting scale 34.

Figure 4:
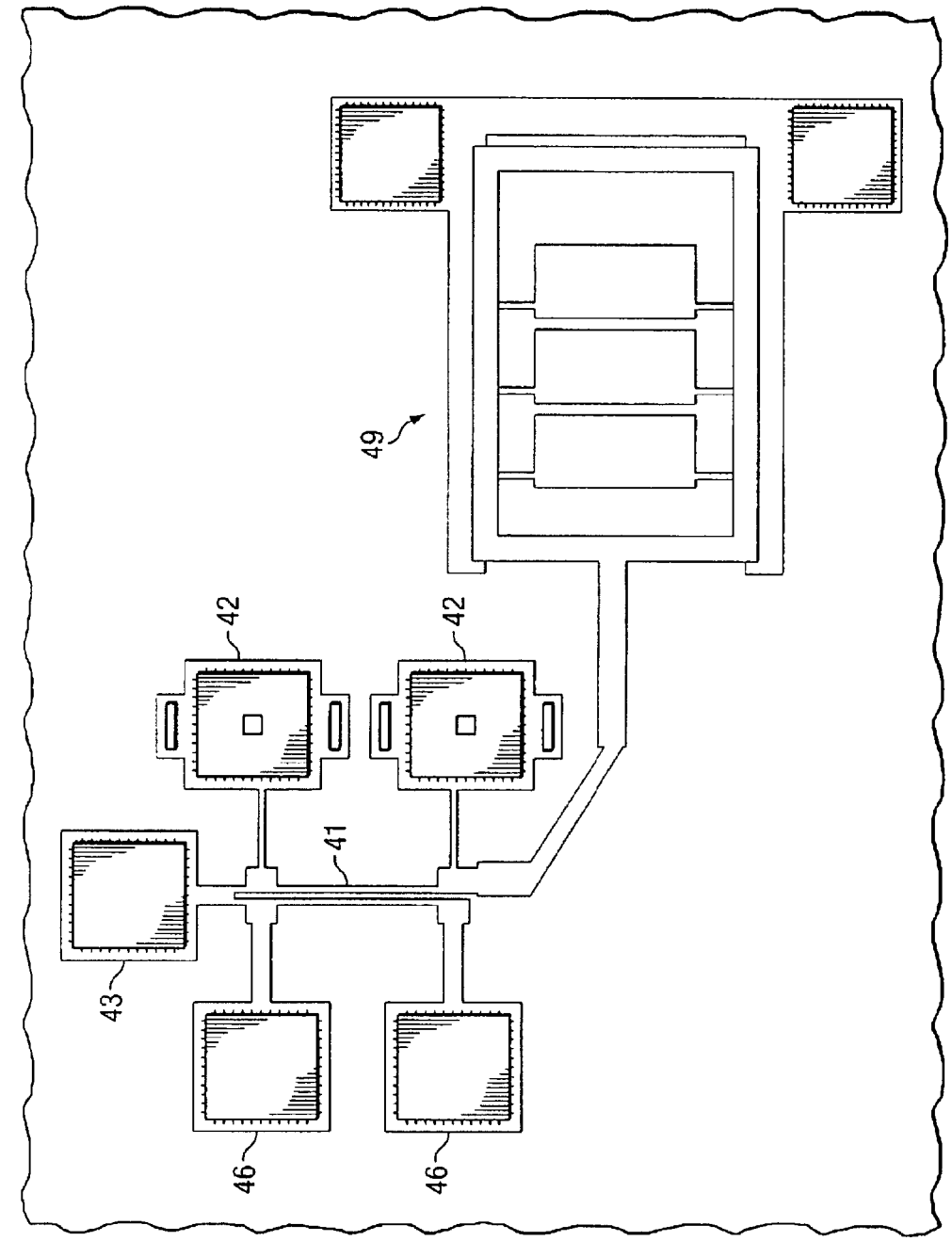
FIG. 4 illustrates a sensor with a double-arm beam and an on-chip actuator.

FIG. 4 illustrates a sensor 40 having a double-arm beam, similar to that of sensor 20. However, sensor 40 includes an on-chip actuator 49. Actuator 49 is attached to the right arm of beam 41, and operates so as to pull that arm of beam 41 to the right. Pads 42, 43, and 46 are similar in structure and operation to the corresponding pads of FIG. 2.

Figure 5:
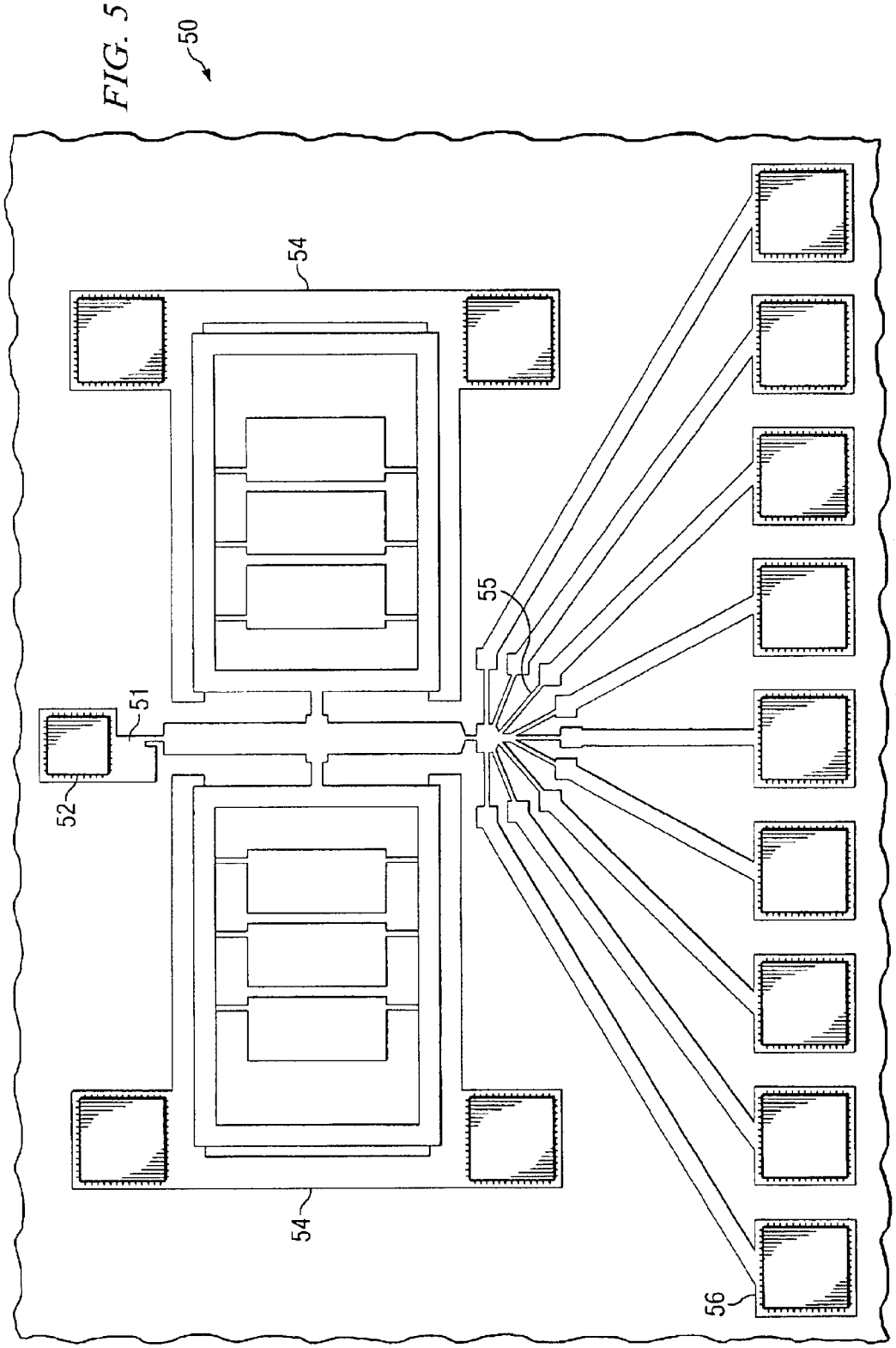
FIG. 5 illustrates a sensor with two on-chip actuators and configured for capacitive measurement.

FIG. 5 illustrates an alternative method for measuring crack propagation. As in the other embodiments, beam 51 cantilevered and has a fixed end attached to pad 52. Although the portion of beam 51 near the fixed end is made from the material of interest, the portion of beam 51 near the free end may be made from a different material. This portion of beam 51 need not be made from the material of interest as its function is to provide greater registration of movement of the free end of beam 51 in response to applied stress.

An actuator 54 is placed on either side of the free end of beam 51. Each actuator 54 is operable to apply force in a horizontal direction that opposes the other. As beam 51 moves, the narrowed end ("needle") of beam 51 passes over a capacitance meter 55. The end of beam 51 acts as one plate of a capacitor, and meter 55 has a series of "fins" that act as the second plate of the capacitor. As the needle end of beam 51 moves across meter 55, the capacitance is measured. Electrical connections run from each meter 55 to electrical pads 56. The applied voltage at the fixed end of beam 51 or via the pads 56 are appropriate for measuring capacitance between the free end of beam 51 and the meter 55.

In alternative embodiments, a capacitance measurement system may be used with a feedback loop to actuators 54 to maintain a fixed position of needle 51a. The capacitive measurement configuration of FIG. 5 could also be implemented with only a single actuator.

The various embodiments described above are each implementations of a method of using MEMS sensors that incorporate a material of interest that is monitored for stress corrosion cracking. The resulting cracking is measured electrically. In this manner, the effects of both stress and the environment can be monitored.

When the device is stressed and placed in situ, the effects of stress on the beam mimic those of an actual structural element. The corrosion on the beam is the same as on the actual element. In this manner, the effects of both stress and the environment on an actual structural element are monitored. The sensor stress can be applied and measurements can be made "on line", in the sense that electrical connections can be maintained while the sensor is placed in the environment of interest.

What is claimed is:

1. A MEMS sensor for measuring stress corrosion cracking of a material of interest, comprising:
    a substrate;
    an electrically conductive cantilever beam fabricated upon the substrate, the beam having a fixed end attached to the substrate and having a free end, and the beam being made from the material of interest;
    at least two conductive pads fabricated on the subtrate adjacent the length of the beam; and
    conductive leads for electrically connecting the conductive pads to the beam;
    wherein the beam is notched to encourage cracking to occur at a predetermined location on the beam.

2. A MEMS sensor for measuring stress corrosion cracking of a material of interest, comprising:
    a subtrate;
    an electrically conductive cantilever beam fabricated upon the subtrate, the beam having a fixed end attached to the subtrate and having a free end, and the beam being made from the material of interest;
    at least two conductive pads fabricated on the subtrate adjacent the length of the beam; and conductive leads for electrically connecting the conductive pads to the beam;

further comprising a scale fabricated at the free end of the beam.

3. A MEMS sensor for measuring stress corrosion cracking of a material of interest, comprising:

a substrate;

an electrically conductive beam fabricated above and spaced over the substrate, the beam having a fixed end attached to the substrate and having a free end, and the beam being made from the material of interest or an analogous material;

wherein the beam is spaced over the substrate such that the free end of the beam may move in a substantially horizontal plane parallel to the surface of the substrate;

a pair of conductive pads, one attached to each end of the beam, for measuring the resistance along the beam.

4. The sensor of claim 3, further comprising at least one actuator fabricated on the substrate, operable to apply stress to the beam.

5. The sensor of claim 4, wherein the actuator moves the beam horizontally over the surface of the substrate.

6. The sensor of claim 3, wherein the beam is split lengthwise for a distance from the free end of the beam into two arms.

7. The sensor of claim 6, further comprising a second pair of conductive pads, such that the resistance along both arms of the beam may be measured.

8. The sensor of claim 3, wherein the beam is notched to encourage cracking to occur at a predetermined location on the beam.

9. The sensor of claim 3, further comprising a scale fabricated at the free end of the beam.

10. The sensor of claim 3, wherein at least one of the conductive pads is moveable across the substrate in response to movement of the beam.

11. The sensor of claim 3, wherein at least one of the conductive pads is fixed to the substrate.

12. A method of measuring stress corrosion cracking of a material of interest, comprising the steps of:

placing a MEMS sensor in an environment of interest, the MEMS sensor having a substrate, a cantilevered beam with a free end and a fixed end attached to the substrate, and having electrical connections to the beam to at least two points along the length of the beam;

wherein the beam is made from the material of interest;

applying stress to the beam;

exposing the beam to environmental corrosion; and measuring the electrical resistance along the length of the beam.

13. The method of claim 12, wherein the step of applying stress is performed with at least one actuator integrated onto the substrate.

14. The method of claim 13, further comprising the step of notching the beam to encourage cracking to occur at a predetermined location on the beam.

15. The method of claim 13, wherein the step of applying stress is performed such that the beam moves horizontally across the substrate.

16. The method of claim 13, wherein the beam is divided into two arms extending from the fixed end of the beam, and wherein the step of applying stress is performed such that stress is applied to one of the arms.

17. The method of claim 13, wherein the beam has a single arm, to which stress is applied and whose resistance is measured.

18. A MEMS sensor for measuring stress corrosion cracking of a material of interest, comprising:

a subtrate;

a beam fabricated upon the substrate, the beam having a fixed end attached to the substrate and having a free end wherein at least a portion of the length of the beam being made from the material of interest or an analogous material;

wherein at least a portion of the beam at the free end is made from or has attached to, an electrically conductive material;

wherein the beam is spaced over the substrate such that the free end of the beam may move in a substantially horizontal plane parallel to the surface of the substrate; and a capacitance meter fabricated adjacent the free end of the beam and operable to measure the capacitance between the free end of the beam and the meter.

19. The sensor of claim 18, further comprising at least one actuator fabricated on the substrate, operable to apply force to the beam in a horizontal direction.

20. The sensor of claim 18, wherein the beam is entirely made from the material of interest or the analogous material.

21. The sensor of claim 19 wherein the actuator moves the beam horizontally over the surface of the substrate.

22. A method of measuring stress corrosion cracking of a material, comprising the steps of:

placing a MEMS sensor in an environment of interest, the MEMS sensor having a substrate, a cantilevered beam with a free end and a fixed end attached to the substrate, and having an electrical connection to the beam;

wherein at least a portion of the beam is made from the material;

applying stress to the beam;

exposing the beam to environmental corrosion;

placing a capacitance meter near the free end of the beam; and measuring the electrical capacitance between the free end of the beam and the capacitance meter.

23. The method of claim 22, wherein the step of applying stress is performed with at least one actuator integrated onto the substrate.

* * * * *